United States Patent [19]
Dahlin et al.

[11] Patent Number: 5,300,769
[45] Date of Patent: Apr. 5, 1994

[54] METHOD AND SYSTEM OF COMPENSATING FOR SIGNAL ARTIFACTS IN A FIBER-OPTIC SENSING SYSTEM

[75] Inventors: Jeffrey J. Dahlin, Bothell; John F. Holic, Jr., Seattle; William G. Lundell, Redmond; Steven B. Duke, Bothell, all of Wash.; Jeffrey B. Yim, Honolulu, Hi.

[73] Assignee: Abbott Laboratories, Abbott Park, Ill.

[21] Appl. No.: 999,495

[22] Filed: Dec. 29, 1992

[51] Int. Cl.$^5$ .................... G01N 33/48; A61B 5/00
[52] U.S. Cl. .................... 250/227.23; 250/227.21; 356/39; 356/41; 128/634
[58] Field of Search .............. 250/227.21, 227.23, 250/226; 356/39, 40, 41; 128/634, 637; 385/12, 13

[56] References Cited

U.S. PATENT DOCUMENTS

| | | | |
|---|---|---|---|
| 4,652,744 | 3/1987 | Bowers et al. | 250/227.27 |
| 4,713,538 | 12/1987 | Theocharous | 250/227.23 |
| 4,907,857 | 3/1990 | Giuliani et al. | 350/96.29 |
| 4,925,268 | 5/1990 | Iyer et al. | 350/96.29 |
| 5,000,901 | 3/1991 | Iyer et al. | 264/299 |
| 5,047,627 | 9/1991 | Yim et al. | 250/227.23 |
| 5,098,659 | 3/1992 | Yim et al. | 422/82.07 |
| 5,119,463 | 6/1992 | Vurek et al. | 385/129 |
| 5,127,077 | 6/1992 | Iyer et al. | 385/116 |

*Primary Examiner*—David C. Nelms
*Assistant Examiner*—John R. Lee
*Attorney, Agent, or Firm*—Christensen, O'Connor, Johnson & Kindness

[57] ABSTRACT

A method and system for controlling the intervals during which light signals are sampled in a fiber-optic sensing system compensates for signal artifacts that are caused by movement of the fiber-optic waveguide during the sampling. The method and system sample the light signals at intervals that are shorter than the intervals during which displacement of the optical waveguide occurs in normal use. The short-sampling intervals result in the individual sampling of different wavelengths of light being exposed to the same changes in transmission characteristics of the optical waveguide which causes signal artifacts. Accordingly, when subsequent processing of the collected signals occurs, the effects of the signal artifacts are compensated for.

22 Claims, 7 Drawing Sheets

METHOD AND SYSTEM OF COMPENSATING FOR SIGNAL ARTIFACTS IN A FIBER-OPTIC SENSING SYSTEM

FIELD OF THE INVENTION

The present invention relates to fiber-optic sensors of the type that rely upon the transmission of light through optical waveguides to transmit signals from a distal probe to equipment that detects the transmitted light signals.

BACKGROUND OF THE INVENTION

In recent years, fiber-optic chemical sensors, sometimes called optrodes, have been developed to detect the presence and monitor the concentration of various analytes, including oxygen, carbon dioxide, and hydrogen ions (i.e., pH) in liquids and in gases. Such sensors are based on the recognized phenomenon that the absorbance, and in some cases luminescence, that is, the phosphorescence or fluorescence of certain indicator molecules, are specifically perturbed in the presence of specific analyte molecules. The perturbation of the luminescence and/or absorbance profile can be detected by monitoring radiation that is absorbed, reflected, or emitted by the indicator molecule in the presence of a specific analyte.

Fiber-optic sensors relying on these characteristics position the analyte sensitive indicator molecule in a light path at a desired measurement site. Typically, the optical fiber transmits electromagnetic radiation from a light source to the indicator molecule, and the reflectance from or absorption of light by the indicator molecule gives an indication of the gaseous or ionic concentration of the analyte. Alternatively, for monitoring other analytes such as oxygen, the optical fiber transmits electromagnetic radiation to the indicator molecule, exciting it into a type of luminescence, for instance phosphorescence, and the level and/or duration of phosphorescence by the indicator molecule serves as an indication of the concentration of that gas in the surrounding fluid. In the prior art sensors, the indicator molecules are typically disposed in a sealed chamber at the distal end of an optical fiber, and the chamber walls are permeable to the analyte of interest.

In view of the importance of accurately measuring blood gas parameters such as carbon dioxide, oxygen, and pH, there is an existing need to provide a fiber-optic sensing system that provides accurate and timely information in actual use. The sensing system should be immune to or compensate for signal artifacts that can be caused by external influences. While prior sensing systems may perform adequately under controlled environments, such as bench scale tests, when animal tests or clinical tests on humans are conducted, the reliability and performance can be noticeably different. Identifying and addressing the sources of changes in the performance of the system when going from bench scale to clinical scale testing will be critical to the development of such sensing systems.

SUMMARY OF THE INVENTION

The present invention is based in part on applicants' discovery that movement or loads applied to optical waveguides in a fiber-optic sensing system during transmission of light signals therethrough causes signal artifacts that can result in unreliable and unpredictable measurements of analytes. Movement of the optical waveguides can occur when operators step away from the equipment or come in contact with the optical waveguides. Movement by the patient can also result in displacement of the optical waveguide. The signal artifacts caused by movement of the optical waveguide are believed to result from the changes in the transmission characteristics of the optical waveguide caused by the movement. The present invention also relates to a method and apparatus described herein that serve to compensate for such signal artifacts and the effects they have on the accuracy of the resulting measurement.

The method of the present invention compensates for signal artifacts in a fiber-optic sensor for monitoring parameters that include a distal probe, source of light signals of a first wavelength, source of light signals of a second wavelength, at least one optical waveguide for transmitting primary light signals from the source of light signals of a first wavelength, and the source of light signals of a second wavelength to the distal probe. The optical waveguide also transmits secondary light signals from the distal probe to at least one sensor for detecting the secondary light signals. The secondary light signals correspond to the response of the probe to the respective primary light signals. The method includes sampling the primary light signal from the source of light signals of a first wavelength (or the secondary light signals from the probe) over a first interval and sampling the primary light signal from the source of light signals of a second wavelength (or the secondary light signals from the probe) over a second interval, wherein the sum of the first interval and the second interval is less than intervals over which displacement of the optical waveguide occurs.

In another aspect, the present invention is a system for controlling the sampling of light signals utilized by a sensor for monitoring a parameter, such as a chemical parameter, the sensor including a distal probe including an optical waveguide. Light signals of a first wavelength are absorbed by the probe to an extent dependent upon the amount of analyte present and light signals of a second wavelength are transmitted (i.e., absorbed to a negligible amount which is not affected by the amount of analyte present) by the probe. In one embodiment of the probe, the light signals of a first wavelength that are not absorbed by the probe and the light signals of a second wavelength transmitted through the probe are reflected by a reflecting material back into the optical waveguide. A source of light signals of the first wavelength is optically coupled to the probe through a first optical pathway and a first photodetector is provided in the first optical pathway for detecting the amount of light signal emitted by the source of light signals of the first wavelength. The first photodetector produces a first electric signal that depends on the amount of the light signal of a first wavelength emitted by the light source. A second photodetector is provided in the first optical pathway for detecting the light signals of the first wavelength attenuated by the probe and producing a second electric signal that depends on the amount of attenuated light signal which is a function of the amount of the light signal of the first wavelength absorbed by the probe. A source of light signals of the second wavelength is optically coupled to the probe through the first optical pathway. The first photodetector detects the amount of the light signal of the second wavelength emitted by the light source and produces a third electric signal that depends on the amount of light signal of the second wavelength emitted by the light source. The second photodetector detects the light signal of the second wavelength transmitted by the probe and produces a fourth electric signal that depends on the amount of the light signal of the second wavelength transmitted by the probe. The first photodetector also detects light signals in the first optical pathway when the source of light signals of the first and second wavelengths are not emitting. In response to the detected light, the first photodetector produces a fifth electric signal that depends on the electronic offsets of the first photodetector circuit, and the first signal-to-frequency converter described below, and ambient light incident on the sensor. The second photodetector also detects light signals in the first optical pathway when the source of light signals of the first and second wavelengths are not emitting. In response to the detected light, the second photodetector produces a sixth electric signal that depends on the electronic offsets of the second photodetector circuit, the second signal-to-frequency converter described below, and ambient light incident on the sensor. The system for controlling the sampling of light signals comprises a first signal-to-frequency converter connected to the first photodetector for producing a first, third, and fifth frequency signal dependent upon the first, third, and fifth electric signals from the first photodetector. A second signal-to-frequency converter is connected to the second photodetector for producing a second, fourth, and sixth frequency signal dependent upon the second, fourth, and sixth electric signals from the second photodetector. The system includes a first counter for sampling the first frequency signal produced by the first signal-to-frequency converter over a first interval, a second counter for sampling the third frequency signal produced by the first signal-to-frequency converter over a second interval, a third counter for sampling the second frequency signal produced by the second signal-to-frequency converter over a first interval, and a fourth counter for sampling the fourth frequency signal produced by the second frequency converter over a second interval. During a third interval when the light source of the first wavelength and the light source of the second wavelength are not emitting, first and second counters sample the fifth frequency signal produced by the first signal-to-frequency converter. Also during this same third interval, the second and fourth counters sample the sixth frequency signal produced by the second signal-to-frequency converter. The sum of the respective first interval, second interval and third interval is less than intervals during which the optical waveguide could be displaced during the normal use. A timer is connected to the first, second, third, and fourth counters and the sources of light signals for controlling the length of the first interval, second interval, and third interval.

Ambient light incident on the probe can be transmitted to the second photodetector by the probe. Ambient light can cause signal artifacts by increasing the light detected by the second photodetector which is unrelated to light attenuated by the sensor. The signal artifact is manifested as increases in the second and fourth electrical signals produced by the second photodetector. The present invention compensates for the ambient light by use of the sixth electrical signal produced by the second photodetector. As mentioned above, the sixth electrical signal is produced during an interval in which no internal light source of the present system is active. Therefore the sixth electrical signal is caused solely by a small electrical offset and by variable ambient light. The second and fourth electrical signals are both influenced by the ambient light to a degree nearly equal to the sixth electrical signal. Because of this, the sixth electrical signal is used in the present system to subtract the unwanted signal artifact from the ambient light on the second and fourth electrical signals. This subtraction of the ambient light artifact represented by the sixth electrical signal eliminates the effects of ambient light on the desired light signals attenuated by the sensor.

In addition to other things, the present invention provides a fiber-optic sensing system and method that compensate for the effect of signal artifacts caused by a change in the transmission characteristics of an optical waveguide when the waveguide is displaced or exposed to an external load.

BRIEF DESCRIPTION OF THE DRAWINGS

The advantages of this invention will become more readily apparent as the same becomes better understood by reference to the following detailed description when taken in conjunction with the accompanying drawings, wherein.

DETAILED DESCRIPTION OF THE PREFERRED EMBODIMENT

Figure 1:
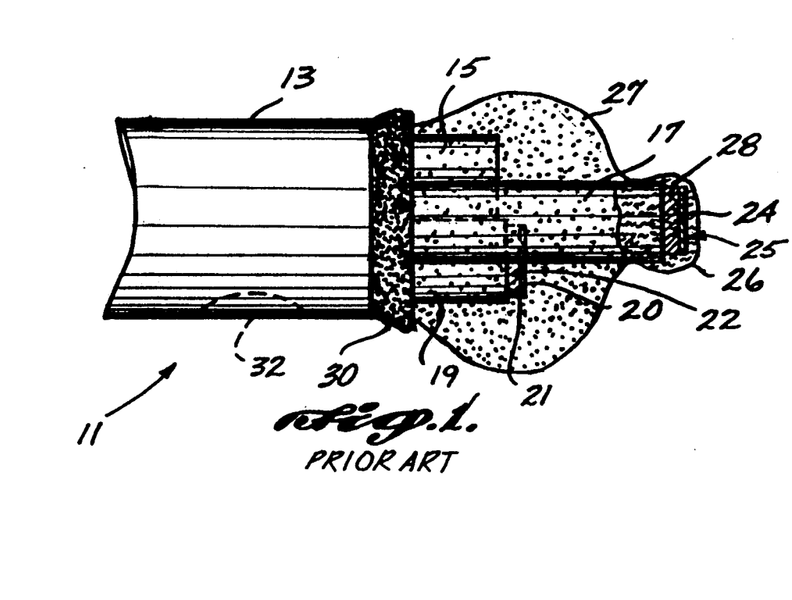
FIG. 1 is a schematic longitudinal view of a fiber-optic probe sensor.
Figure 2:
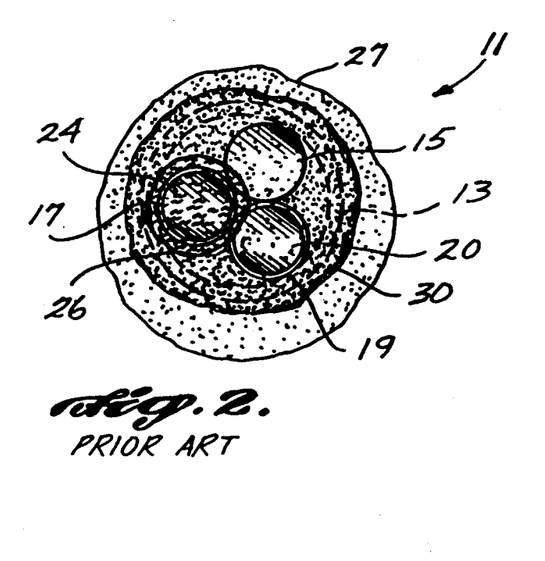
FIG. 2 is an end view of FIG. 1.

One type of fiber-optic sensor that is useful in the method and sensing system of the present invention is described in U.S. Pat. No. 5,047,627, the disclosure of which is incorporated herein by reference. Referring to FIGS. 1 and 2 in the present application, fiber-optic probe sensor 11 of U.S. Pat. No. 5,047,627 is illustrated and described. The numbering convention for FIGS. 1 and 2 of this application correspond to the numbering convention used in the specification and drawings of the '627 patent. The disclosed fiber-optic sensor is for monitoring chemical parameters but it should be understood that the present invention has equal utility for fiber-optic sensors that monitor non-chemical parameters.

Fiber-optic sensor 11 comprises three individual optical fibers 15, 17, and 19 encased in a polyimide sheath 13. More specifically, the three optical fibers are arranged such that their longitudinal axes (the axis generally corresponding to the path of a light signal propagating therein) are parallel and are arranged in an equilateral triangle array. Optical fiber 15 conveys light signals used to sense oxygen ($O_2$) concentration, optical fiber 17 is used to convey light signals for sensing hydrogen ion concentration (pH), and optical fiber 19 is used for conveying light signals for sensing carbon dioxide ($CO_2$) concentration.

The distal ends of all three optical fibers are cleaved perpendicularly to their longitudinal axes, and each distal end comprises a substantial planar, circular surface. Disposed upon the circular surface of $CO_2$ optical fiber 19 is a substantially cylindrical $CO_2$ pellet 21 (i.e., a sensor for $CO_2$ in pellet form) having a diameter approximately equal to that of $CO_2$ optical fiber 19. $CO_2$ pellet 21 includes a $CO_2$ analyte sensitive matrix material 22 and a thin film of reflective material 20. $CO_2$ analyte sensitive matrix material 22 absorbs light signals having certain wavelengths to a degree dependent on the concentration of $CO_2$ pellet 21. The thin film of reflective material 20 is incorporated onto the distal circular surface of $CO_2$ pellet 21, is substantially concentric with a cylindrical surface of the $CO_2$ pellet 21, and is situated such that a light signal propagated through $CO_2$ optical fiber 19 and $CO_2$ pellet 21 is reflected by reflective material 20 back into $CO_2$ optical fiber 19.

Similarly, a cylindrical pH pellet 25 (i.e., a sensor for pH in pellet form) is attached to the distal end of pH optical fiber 17. pH pellet 25 is sized so as to substantially cover the entire circular surface of the distal end of pH optical fiber 17, and includes a pH analyte sensitive material 28 and a thin film of reflective material 24. pH analyte sensitive material 28 absorbs light signals having certain wavelengths to a degree dependent on the concentration of hydrogen ions around pH pellet 25. The thin film of reflective material 24 is incorporated onto the distal circular surface of pH pellet 25, is substantially concentric with the surface of pH pellet 25, and is situated such that a light signal propagated down pH optical fiber 17 and through pH pellet 25 is reflected by reflective material 24 back into pH optical fiber 17.

Still referring to FIGS. 1 and 2, it can be seen that an $O_2$ indicator matrix 27 encapsulates the entire distal ends of $O_2$ optical fiber 15, $CO_2$ optical fiber 19, $CO_2$ pellet 21, and a substantial portion of pH optical fiber 17 that extends beyond polyimide sheath 13. $O_2$ indicator matrix 27 includes an oxygen analyte indicator molecule that when excited by light, produces a response that is dependent upon the oxygen concentration surrounding the $O_2$ indicator matrix 27.

Figure 3:
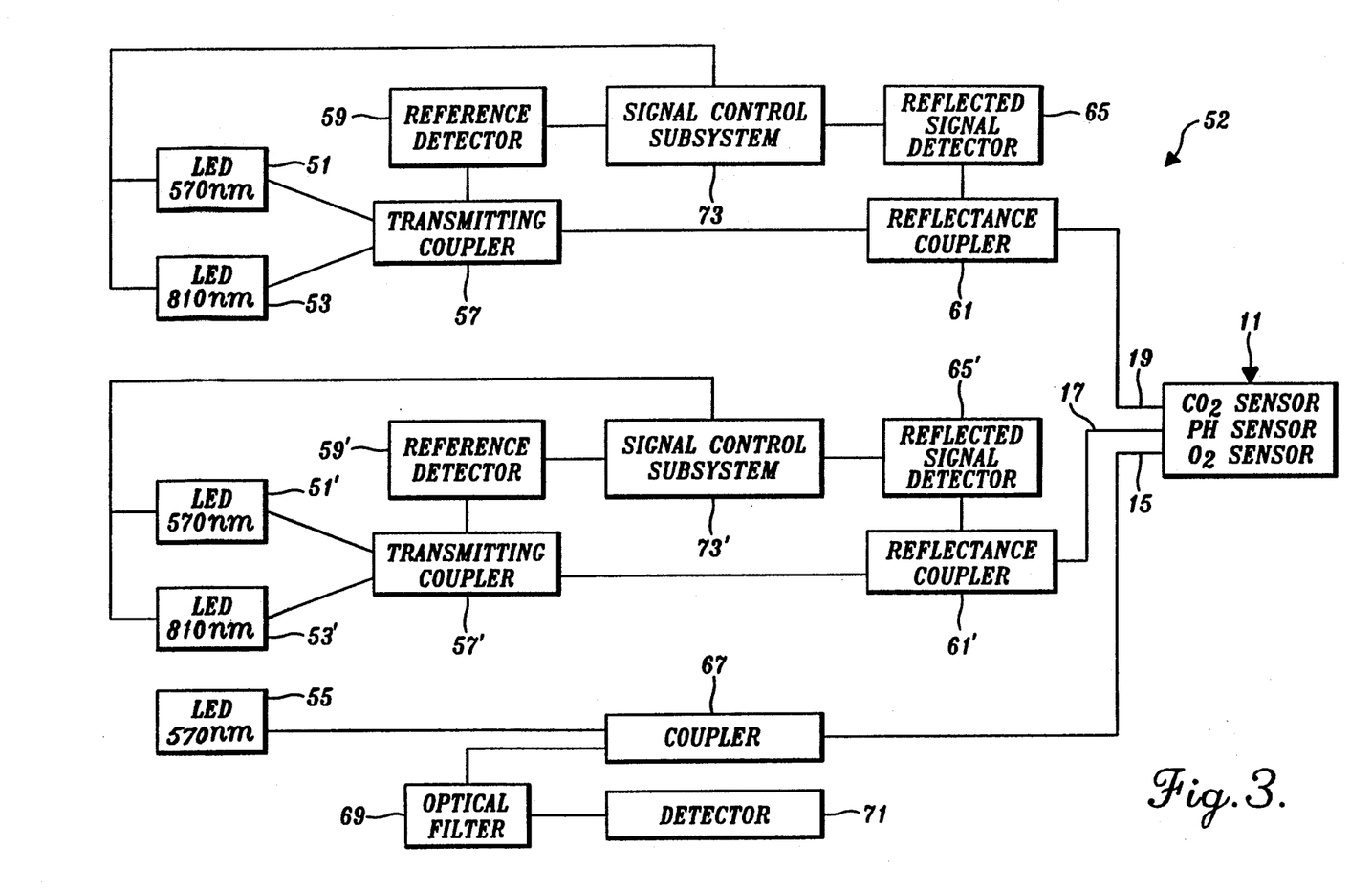
FIG. 3 is a block diagram of a portion of a sensing system using the fiber-optic sensor of FIGS. 1 and 2 to measure $CO_2$, $O_2$, and pH of a fluid.

Referring to FIG. 3, fiber-optic sensor 11 described above and described in more detail in U.S. Pat. No. 5,047,627 can be used in a blood analyte monitoring system. As an exemplary illustration, fiber-optic sensor 11 is integrated into a complete optical physiological blood-gas concentration sensing system 52. Blood gas concentration sensing system 52 comprises two light emitting diodes (LED) light sources 51 and 51' that produce light signals having a wavelength in the green region of the visible spectrum of about 570 nanometers, two LED light sources 53 and 53' that produce light signals having a wavelength in the near infrared (NIR) region of the spectrum of about 810 nanometers, and a third LED light source 55 producing light having a wavelength of about 570 nanometers. In blood gas concentration sensing system 52, LEDs 51 and 53 are used to determine $CO_2$ concentration, LEDs 51' and 53' are used to determine pH levels, and LED 55 is used to determine $O_2$ concentration.

In blood gas concentration sensing system 52, LEDs 51 and 53 each generate light that propagates along an optical pathway into transmitting coupler 57 where each of the light signals can be split into two separate optical pathways. The light signal in one optical pathway is transmitted to reference detector 59 and the light signal in the other optical pathway is transmitted to reflectance coupler 61. Reference detector 59 produces reference electric signals in response to the amplitude of light signals detected. The reference electric signals are transmitted to signal control subsystem 73 formed in accordance with the present invention and are used to compensate for variations in the output of LEDs 51 and 53.

The output of LED 51 transmitted to reflectance coupler 61 is transmitted to the distal end of $CO_2$ optical fiber 19, where the light signal is partially absorbed by $CO_2$ analyte sensitive matrix 22 and $CO_2$ pellet 21 to a degree that depends on the concentration of $CO_2$ around $CO_2$ pellet 21. The resulting attenuated light signal is reflected by reflective material 20 and propagated back as the return reflected light signal into $CO_2$ optical fiber 19. The absorption of light signals from LED 53 by $CO_2$ pellet 21 is negligible and not affected by $CO_2$ concentration. Accordingly, light signals from LED 53 are transmitted through $CO_2$ analyte sensitive matrix 22 and $CO_2$ pellet 21 and also are reflected back into $CO_2$ optical fiber 19. The return reflected signals from both LED 51 and 53 propagate into reflectance coupler 61 which diverts the return reflected signals into reflected signal detector 65. Reflected signal detector 65 measures the amplitude of the return reflected signal from LED 51 and the amplitude of the return reflected signal from LED 53 and produces signals dependent on the measured amplitudes. The signals produced by reflected signal detector 65 are transmitted to signal control subsystem 73 which is described below in more detail.

The operation of pH sensing portion of blood gas concentration sensing system 52 is similar to the above-described $CO_2$ sensing portion. LEDs 51' and 53' produce light signals that are transmitted into transmitting coupler 57'. Light signals from both LEDs 51' and 53' are each split into separate optical pathways by transmitting coupler 57'. One optical pathway transmits light signals to reference detector 59'. Reference detector 59' produces reference electric signals in response to the amplitude of light signals detected. The reference electric signals are transmitted to signal control subsystem 73 and are used to compensate for variations in output of LEDs 51' and 53'. The other optical pathway transmits light signals to reflectance coupler 61' and onto the distal end of pH optical fiber 17. The light signals from LED 51' are absorbed by pH pellet 25 as a function of hydrogen ion concentration in the fluid around pH pellet 25. The attenuated light signals from LED 51' are reflected back into pH optical fiber 17 by the layer of reflective material 24 in pH pellet 25. The absorption of light signals from LED 53' in pH pellet 25 is negligible and is not affected by the hydrogen ion concentration (pH) of the fluid around pellet 25. Return reflected signals at both wavelengths are conveyed by pH optical fiber 17 into reflectance coupler 61' which diverts the return reflected signals into reflected signal detector 65'. Reflected signal detector 65' measures the amplitude of the return reflected signals from LEDs 51' and 53' and produces signals dependent on the measured amplitudes. The signals produced by reflected signal detector 65' are transmitted to signal control subsystem 73' which is described below in more detail.

The operation of the $O_2$ sensing portion of blood gas concentration sensing system 52 is somewhat different than the $CO_2$ portion and pH portion. The light signals produced by LED 55 travel through coupler 67 and into $O_2$ optical fiber 15. At the distal end of $O_2$ optical fiber 15, the signal excites $O_2$ analyte indicator matrix 27 to phosphoresce. The resulting phosphorescent light signal is conveyed by $O_2$ optical fiber 15 back to coupler 67. From coupler 67, the signal is diverted through an optical passband filter 69. The filtered phosphorescent light signal is monitored by a detector 71. By measuring the phosphorescence decay time of this light signal, the oxygen gas concentration around fiber-optic sensor 11 can be determined. Generally, the higher the concentration of $O_2$ to which fiber-optic sensor 11 is exposed, the faster the phosphorescence is quenched.

Figure 4:
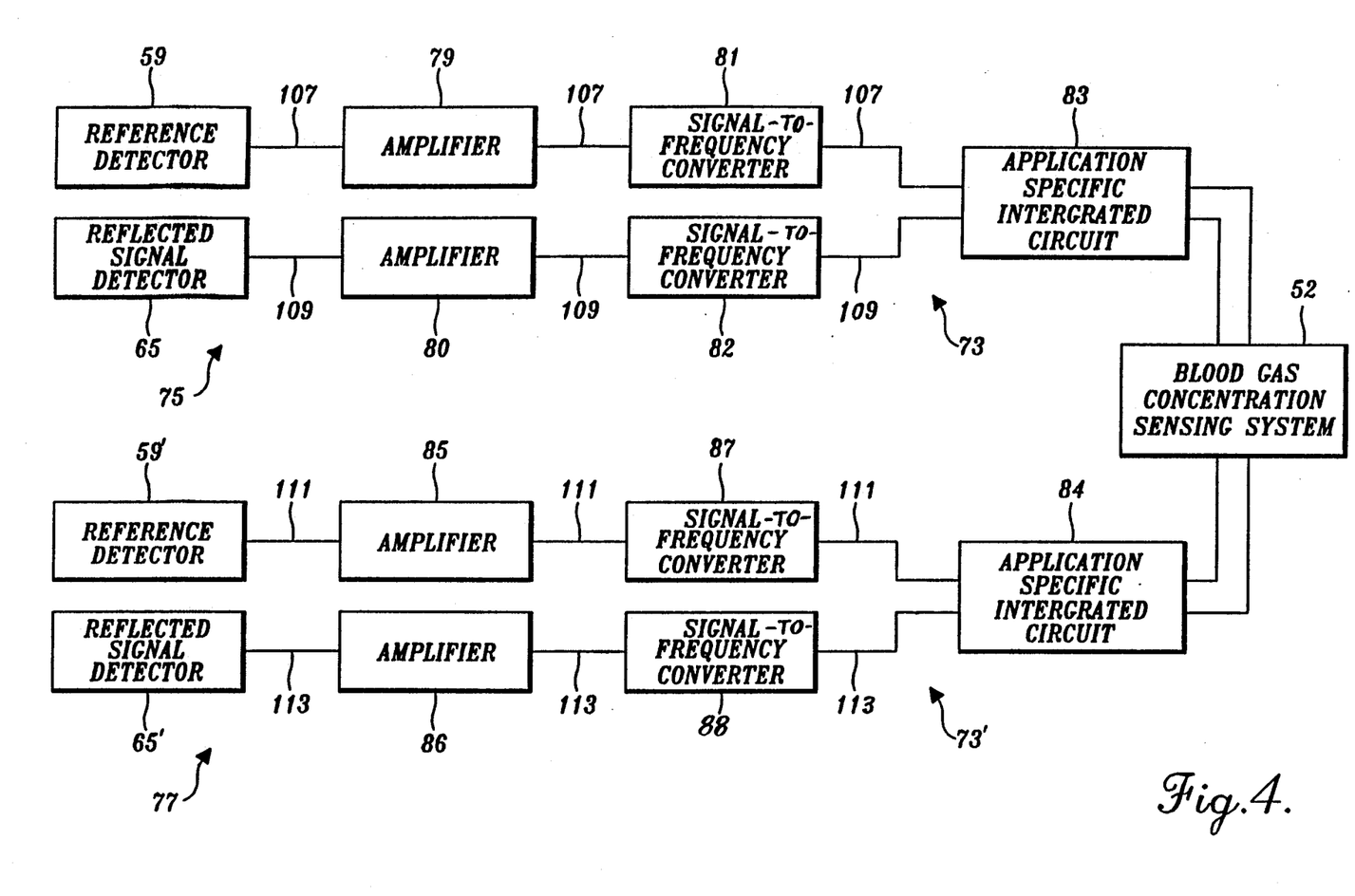
FIG. 4 is a block diagram of a signal control subsystem that is a component of a sensing system formed in accordance with the present invention to measure $CO_2$, $O_2$, and pH of a fluid.

Referring to FIG. 4, signal control subsystem 73 for the $CO_2$ portion of blood gas concentration sensing system 52 includes signal pathway 75 (for LED 51 and 53) and signal control subsystem 73' for pH portion of blood gas concentration sensing system includes signal pathway 77 (for LED 51' and 53'). Signal pathway 75 carries time-multiplexed signals generated by reference detector 59 on reference signal channel 107 to amplifier 79 and time-multiplexed signals generated by reflected signal detector 65 on reflected signal channel 109 to amplifier 80. Amplifiers 79 and 80 amplify the input signals. The outputs of amplifiers 79 and 80 are transmitted to respective signal-to-frequency converters 81 and 82. Signal-to-frequency converters 81 and 82 convert the signals from amplifiers 79 and 80 to frequency signals. The output frequency signals from signal-to-frequency converters 81 and 82 are time-multiplexed and transmitted to an application specific integrated circuit 83 that is described below in more detail.

Signal pathway 77 is similar to signal pathway 75. Output signals from reference signal detector 59' on reference signal channel 111 and reflected signal detector 65' on reflected signal channel 113 are transmitted to respective amplifiers 85 and 86 which produce output signals that are greater than and dependent upon the input signals. Output signals from amplifiers 85 and 86 are transmitted to respective signal-to-frequency converters 87 and 88 where they are converted to frequency signals. The output frequency signals from signal-to-frequency converters 87 and 88 are transmitted to an application specific integrated circuit 84.

Figure 5:
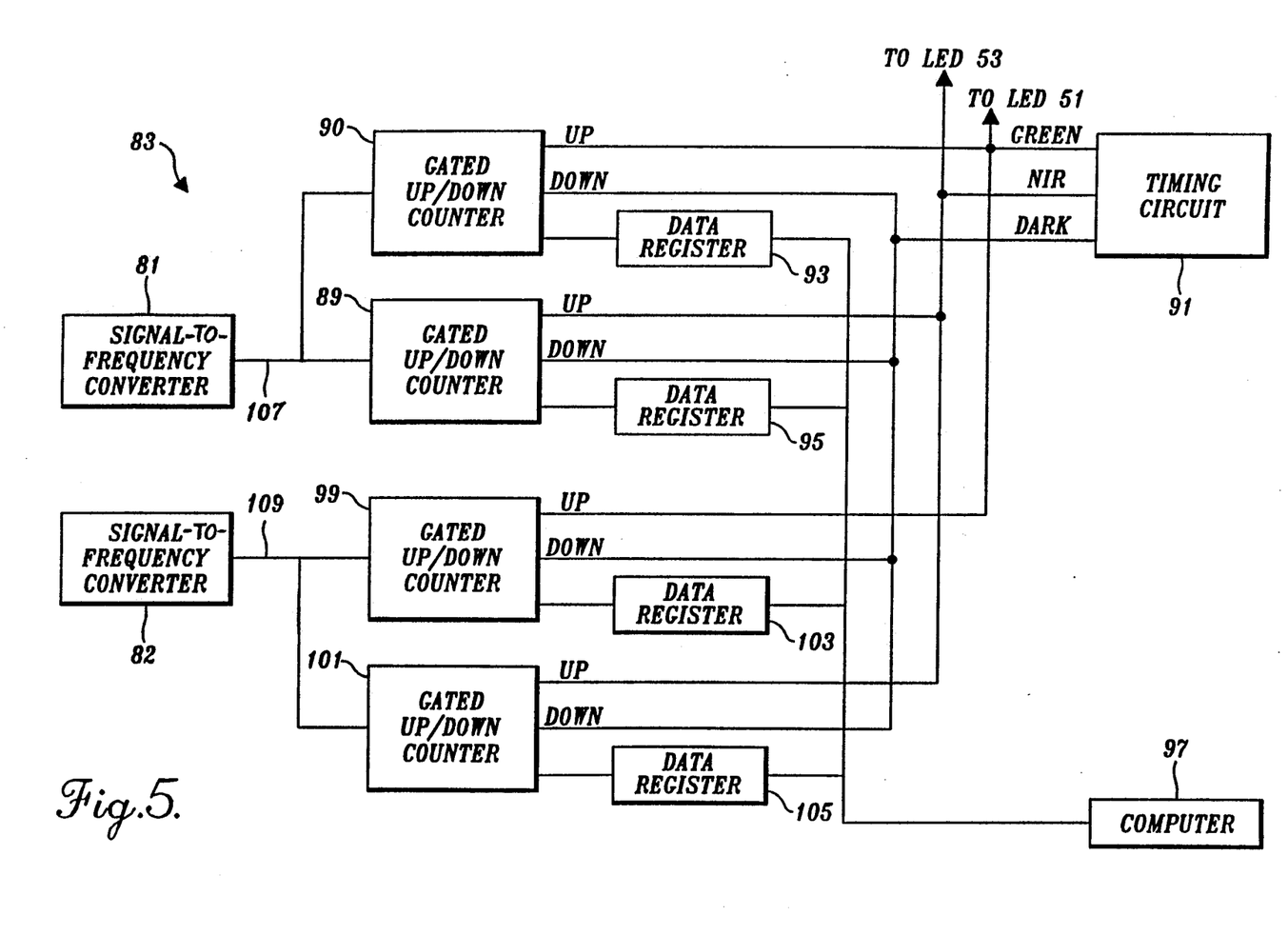
FIG. 5 is a schematic of an application specific integrated circuit that is a component of the signal control subsystem of FIG. 4.

Referring additionally to FIG. 5, application specific integrated circuit 83 (illustrated in conjunction with signal-to-frequency converters 87 and 88, and computer 97) receives output signals from signal-to-frequency converters 81 and 82 on reference signal channel 107 and reflected signal channel 109. Reference signal channel 107 is time-multiplexed to a gated up-down counter 90 and a gated up-down counter 89. Gated up-down counter 90 receives frequency signals corresponding to reference light signals from LED 51 detected by reference detector 59. Gated up-down counter 89 receives frequency signals corresponding to reference light signals from LED 53 detected by reference detector 59. Gated up-down counters 90 and 89 count the waveforms of the respective frequency signals on reference signal channel 107 during intervals of time controlled by timing circuit 91. Periodically, the counts accumulated in counters 90 and 89 and stored in respective data registers 93 and 95 and the counters are reset to zero. When this occurs, computer 97 is signaled to read the data stored in data registers 93 and 95 for further processing.

Reflected signal channel 109 in application specific integrated circuit 83 is similar to reference signal channel 107. Reflected signal channel 109 is time-multiplexed to gated up-down counter 99 and gated up-down counter 101. Gated up-down counter 99 receives the frequency signal corresponding to the light signal from LED 51 reflected by the probe and detected by reflected signal detector 65 during intervals of time controlled by timing circuit 91. Gated up-down counter 101 receives the frequency signal corresponding to the light signal from LED 53 reflected by the probe and detected by reflected signal detector 65 during intervals of time controlled by timing circuit 91. As with gated up-down counters 90 and 89, periodically, the counts accumulated in counters 99 and 101 are stored in respective data registers 103 and 105, and the counters are reset to zero. When this occurs, computer 97 is signaled to read data stored in data registers 103 and 105 for further processing.

Figure 6:
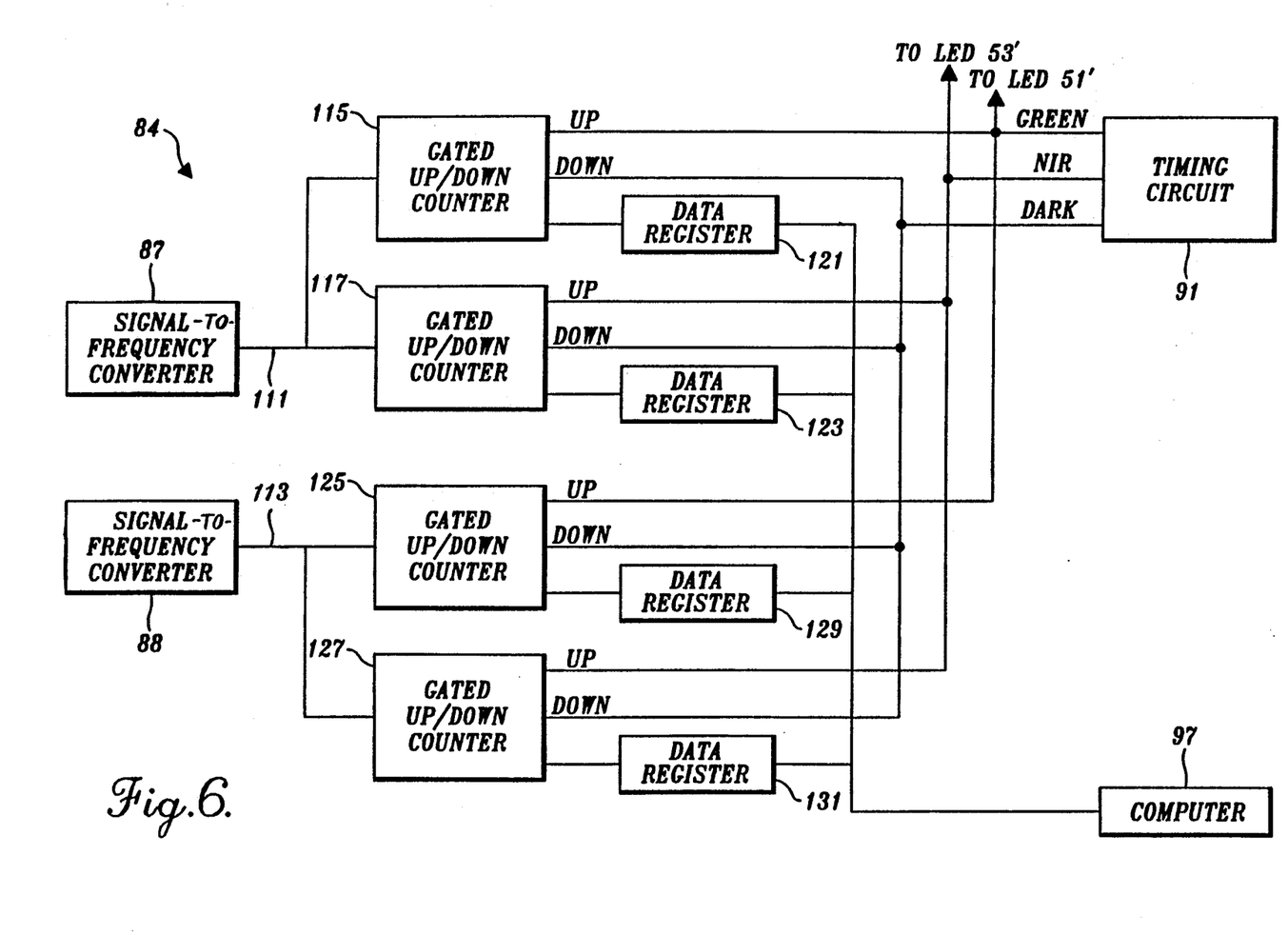
FIG. 6 is a schematic of an application specific integrated circuit that is a component of the signal control system of FIG. 4.

Referring to FIGS. 4 and 6, application specific integrated circuit 84 (illustrated in conjunction with signal-to-frequency converters 87 and 88, and computer 97) receives output signals from signal-to-frequency converters 87 and 88 on respective reference signal channel 111 and reflected signal channel 113. Reference signal channel 111 is time-multiplexed to gated up-down counter 115 and gated up-down counter 117. Gated up-down counter 115 receives frequency signals corresponding to reference light signals from LED 51' detected by reference detector 59'. Gated up-down counter 117 receives frequency signals corresponding to reference light signals from LED 53' detected by reference detector 59'. Gated up-down counters 115 and 117 count the waveforms of the respective signals on reference signal channel 111 during intervals of time controlled by timing circuit 91. Periodically, the counts accumulated in counters 115 and 117 are stored in respective data registers 121 and 123 and the counters are reset to zero. When this occurs, computer 97 is signaled to read the data stored in data registers 121 and 123 for further processing.

Reflected signal channel 113 in application specific integrated circuit 84 is similar to reference signal channel 111. Reflected signal channel 113 is time-multiplexed to gated up-down counter 125 and gated up-down counter 127. Gated up-down counter 125 receives the frequency signal corresponding to the light signal from LED 51' reflected by the probe and detected by reflected signal detector 65' during intervals of time controlled by timing circuit 91. Gated up-down counter 127 receives the frequency signal corresponding to the light signal from LED 53' reflected by the probe and detected by reflected signal detector 65' during intervals of time controlled by timing circuit 91. As with gated up-down counters 115 and 117, periodically the counts accumulated in counters 125 and 127 are stored in respective data registers 129 and 131 and the counters are reset to zero. When this occurs, computer 97 is signaled to read the data stored in data registers 129 and 131 for further processing. The intervals over which gated up-down counters 115, 117, 125, and 127 sample their respective frequency signals are described below in more detail. Timing circuit 91 also controls the intervals over which LEDs 51' and 53' are excited. It should be understood that while the present embodiment of the invention has been described with respect to two applications specific integrated circuits 83 and 84, the functions of such applications specific integrated circuits may be combined into one single application specific integrated circuit.

An exemplary mode of operating the $CO_2$ portion of blood-gas concentration sensing system 52 including the signal control subsystem 73 of the present invention is described below. It should be understood that while the embodiment described above includes a probe for sensing oxygen, the method and apparatus of the present invention do not require the presence of the oxygen sensing portion.

In operation, fiber-optic sensor 11 is introduced into a blood vessel using, for example, a catheter. Once positioned within the blood vessel, LED 51 is excited for a first interval. In accordance with the description set forth above, the light signal from LED 51 results in a frequency signal on reference signal channel 107 into application specific integrated circuit 83. In application specific integrated circuit 83, gated up-down counter 90 is enabled by timing circuit 91 and counts up the waveforms of the frequency signal for a first interval. At the end of the first interval, counter 90 is stopped and LED 51 is turned off. LED 53 is then excited and results in a frequency signal on reference signal channel 107 which is received by application specific integrated circuit 83. In application specific integrated circuit 83, gated up-down counter 89 counts up the waveforms of the frequency signal for a second interval that is controlled by timing circuit 91. At the end of the second interval, timing circuit 91 stops the counting by up-down counter 89 and also turns off LED 53. Up-down counters 90 and 89 are then allowed to count down the waveforms during a third interval wherein no signals from LEDs 51 or 53 are on reference signal channel 107. This "dark signal" serves as a means to compensate for electronic offset of the equipment, particularly reference detector 59, reflected signal detector 65, and signal-to-frequency converters 81 and 82. The "dark signal" also serves to compensate for ambient light incident on fiber-optic sensor 11. The process of counting up and down is repeated over a period of time, allowing counts to accumulate. At periodic intervals, the accumulate counts in the gated up-down counters 90 and 89 are stored in respective data registers 93 and 95. The gated up-down counters 90 and 89 are then reset to zero and the counters begin accumulating counts for the next period. Exemplary accumulation periods are about one second.

Gated up-down counters 99 and 101 in application specific integrated circuit 83 operate in a similar manner to gated up-down counters 90 and 89. On reflected signal channel 109, gated up-down counter 99 counts up waveforms during a first interval during which LED 51 is excited. The frequency signal that is counted during the first interval by gated up-down counter 99 corresponds to the light signal that is produced by LED 51 and detected by reflected signal detector 65. The frequency signal that is counted by gated up-down counter 101 during the second interval corresponds to the light signal produced by LED 53 and detected by reflected signal detector 65. The process of counting up and down is repeated over a period of time, allowing counts to accumulate. At periodic intervals, the cumulative counts in the gated up-down counters 99 and 101 are stored in respective data registers 103 and 105. The gated up-down counters 99 and 101 are then reset to zero and the counters begin accumulating counts for the next period. As described above, at periodic intervals computer 97 reads the data in data registers 103 and 105. Exemplary intervals for excitation of LEDs 51 and 53, and darkness, are approximately 4 milliseconds or less. The sampling interval is preferably chosen to be unequal to the interval of maximum ambient light caused by artificial light, e.g., such as from 120 hertz or 100 hertz flickers of fluorescent lamp. All three intervals should be equal in length. Generally, when the intervals for excitation of LEDs 51 and 53, and darkness are about 4 milliseconds or less, it is preferred to enable the counters to count up or down except for the first 200-300 microseconds after an LED change. This delay between turning the LED on or off and starting the counting interval allows the circuitry time to settle to new signal levels. Sampling intervals of the data registers by computer 97 can be about one second and should be a multiple of sum of the first, second, and third intervals so that the same number of count up periods as count down periods are sampled.

Longer or shorter intervals of LED excitation and darkness intervals would be acceptable provided the sampling interval is short enough so that changes in the light intensity due to changes in transmission characteristics of the optical waveguide are negligible. For example, intervals of LED excitation and darkness on the order of 250 milliseconds should be compatible with the present invention.

In the illustrated embodiment of the operation of the signal control subsystem 73, the sequence of LED signals and dark signals is as follows:
1. Green interval. LED 51 excited.
2. Gated up-down counters 90 and 99 allowed to count up beginning 200-300 microseconds after LED 51 excited. Gated up-down counters 89 and 101 hold.
3. LED 51 turned off and count up interval of counters 90 and 99 ends.
4. NIR interval. LED 53 excited.
5. Gated up-down counters 89 and 101 allowed to count up beginning 200-300 microseconds after LED 53 excited. Gated up-down counters 90 and 99 hold.
6. LED 53 turned off and count up interval of counters 89 and 101 ends.
7. Dark interval. Up-down counters 90, 89, 99, and 101 allowed to count down beginning 200-300 microseconds after LED 53 is turned off.
8. Dark interval ends. Up-down counters 90, 89, 99 and 101 hold.
9. LED 51 excited again and steps 1-8 repeated.
10. After steps 1-8 are repeated, a predetermined number of times, cumulative counts are stored in data registers 93, 95, 103 and 105, the counters are reset, the computer is signaled, and the sequence is repeated.

An exemplary mode of operating the pH portion of blood gas concentration sensing system 52 including the signal control subsystem 73' of the present invention, is described below. After positioning a fiber-optic sensor in a blood vessel as described above, LED 51' is excited and results in a frequency signal on reference signal channel 111 into application specific integrated circuit 84. In application specific integrated circuit 84, gated up-down counter 115 is enabled by timing circuit 91 and counts up the waveforms of the frequency signal for a first interval. At the end of the first interval, counter 115 is stopped and LED 51' is turned off. LED 53' is then excited and results in a frequency signal on reference signal channel 111 which is received by application specific integrated circuit 84. In application specific integrated circuit 84, gated up-down counter 117 counts up the waveforms of the frequency for a second interval that is controlled by timing circuit 91. At the end of the second interval, timing circuit 91 stops the counting by up-down counter 117 and also turns off LED 53'. Up-down counters 115 and 117 are then allowed to count down the waveforms during a third interval wherein no signals from LED 51' or 53' are on reference signal channel 111. This "dark signal" serves as a means to compensate for electronic offset of the equipment particularly reference detector 59', reflected signal detector 65, and signal-to-frequency converters 87 and 88. As described above, this "dark signal" also serves to compensate for ambient light incident on fiber-optic sensor 11. The process of counting up and down is repeated over a period of time, allowing counts to accumulate. At periodic intervals the cumulative counts in the gated up-down counters 115 and 117 are stored in respective data registers 121 and 123. The gated up-down counters 115 and 117 are then reset to zero and the counters begin accumulating counts for the next period.

Gated up-down counters 125 and 127 in application specific integrated circuit 84 operate in a similar manner to gated up-down counters 115 and 117. On reflected signal channel 113, gated up-down counter 125 counts up during a first interval during which LED 51' is excited. The frequency signal that is counted during the first interval by gated up-down counter 125 corresponds to the light signal that is produced by LED 51' and detected by reflected signal detector 65'. The frequency signal that is counted by gated up-down counter 127 during the second interval corresponds to the light signal produced by LED 53' and detected by reflected detector signal 65'. The process of counting up and down is repeated over a period of time, allowing counts to accumulate. At periodic intervals, the cumulative counts in the gated up-down counters 125 and 127 are stored in respective data registers 129 and 131. The gated up-down counters 125 and 127 are then reset to zero and the counters begin accumulating counts for the next period. As described above, at periodic intervals computer 97 reads the data in data registers 129 and 131. Exemplary intervals for excitation of LEDs 51' and 53', and darkness is approximately 4 milliseconds, or less, and should be equal in length. Generally, when the intervals for excitation of LEDs 51' and 53' and darkness are about 4 milliseconds or less, it is preferred to enable the counters to count up or count down except for the first 200-300 microseconds after a LED change. This delay between turning the LED on or off and starting the counting interval allows the circuit time to settle to new signal levels. Sampling intervals of data registers 121, 123, 129, and 131 by computer 97 are generally about one second and should be a multiple of the sum of the first, second, and third interval cycle so that the same number of count up periods as count down periods are sampled. Longer or shorter intervals of LED excitation and darkness intervals would be acceptable provided the sampling interval is short enough so that changes in the light intensity due to changes in transmission characteristics of the optical waveguide are negligible. For example, intervals of LED excitation and darkness on the order of 250 milliseconds should be compatible with the present invention.

In the illustrated embodiment of the operation of the signal control subsystem 73', the sequence of LED signals and dark signals is as follows:

1. Green interval. LED 51' excited.
2. Gated up-down counters 115 and 125 allowed to count up beginning 200-300 microseconds after LED 51' excited. Gated up-down counters 117 and 127 hold.
3. LED 51' turned off and count up interval of counters 115 and 125 ends.
4. NIR interval. LED 53' excited.
5. Gated up-down counters 117 and 127 allowed to count up beginning to 200-300 microseconds after LED 53' excited. Gated up-down counters 115 and 125 hold.
6. LED 53' turned off and count up interval of counters 117 and 127 ends.
7. Dark interval. Up-down counters 115, 117, 125 and 127 allowed to count down beginning 200-300 microseconds after LED 53 is turned off.
8. Dark interval ends. Up-down counters 115, 117, 125 and 127 hold.
9. LED 51' excited again and steps 1-8 repeated.
10. After steps 1-8 repeated a predetermined number of times, the cumulative counts are stored in data registers 121, 123, 129 and 131, the counters are reset, the computer is signaled and the sequence is repeated.

Figure 7:
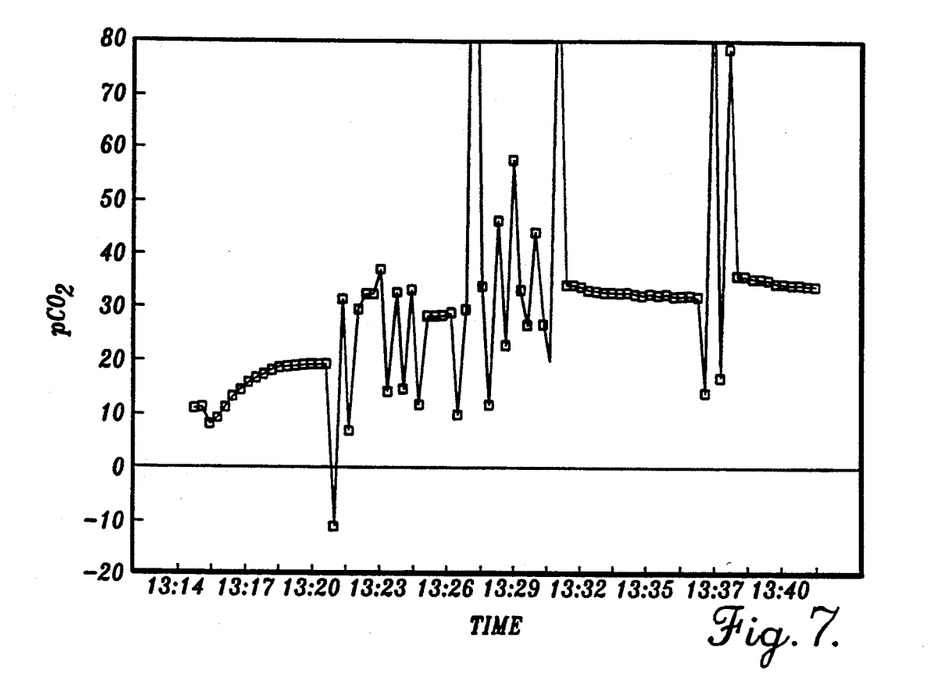
FIG. 7 is a graphical representation of $CO_2$ measurements and the effect of movement of the optical waveguide during such measurements.
Figure 8:
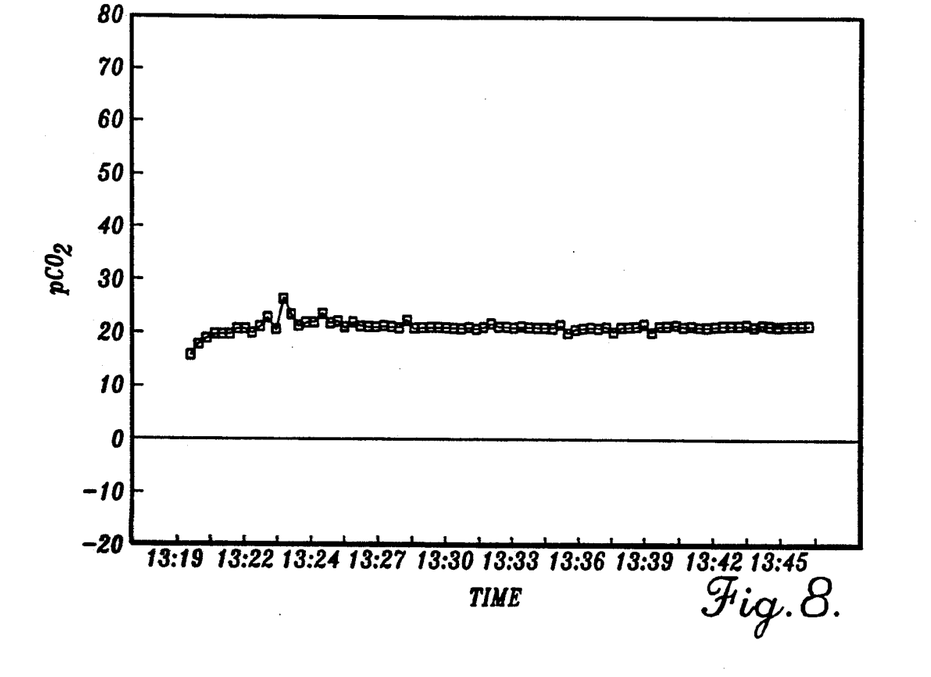
FIG. 8 is a graphical representation of the effectiveness of the method and system of the present invention to compensate for signal artifacts resulting from movement of the optical waveguide.

FIGS. 7 and 8 illustrate the effectiveness of the method and apparatus formed in accordance with the present invention for compensating for signal artifacts that are introduced into optical waveguides by movement thereof during signal sampling. FIG. 7 is a graphical illustration of stable $CO_2$ concentration levels measured during several intervals of movement of the optical waveguide using prior timing sequences that do not compensate for movement of the optical waveguide during signal sampling. The discontinuities in the data correspond to those time intervals when movement of the optical fiber was observed. FIG. 8 is a graphical illustration of stable $CO_2$ concentration levels measured according to the method and apparatus of the present invention over a time period that includes several intervals during which the optical waveguide was displaced during signal sampling. By comparison, the measurement illustrated in FIG. 8 exhibits a significantly reduced number of discontinuities during the intervals when the optical waveguide is displaced.

Figure 9:
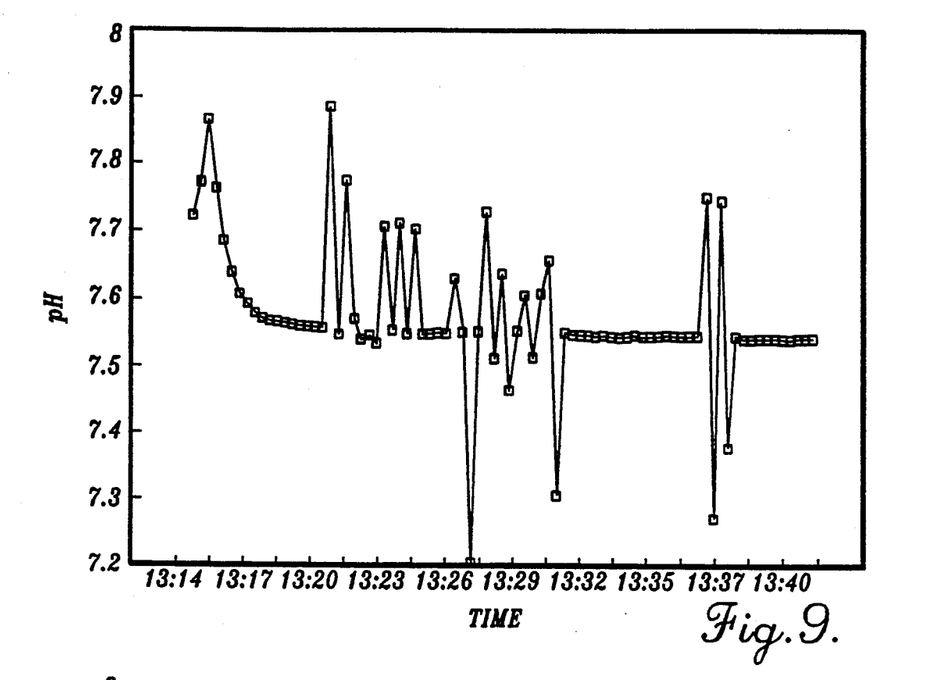
FIG. 9 is a graphical representation of pH measurements and the effect of movement of the optical waveguide during such measurements.
Figure 10:
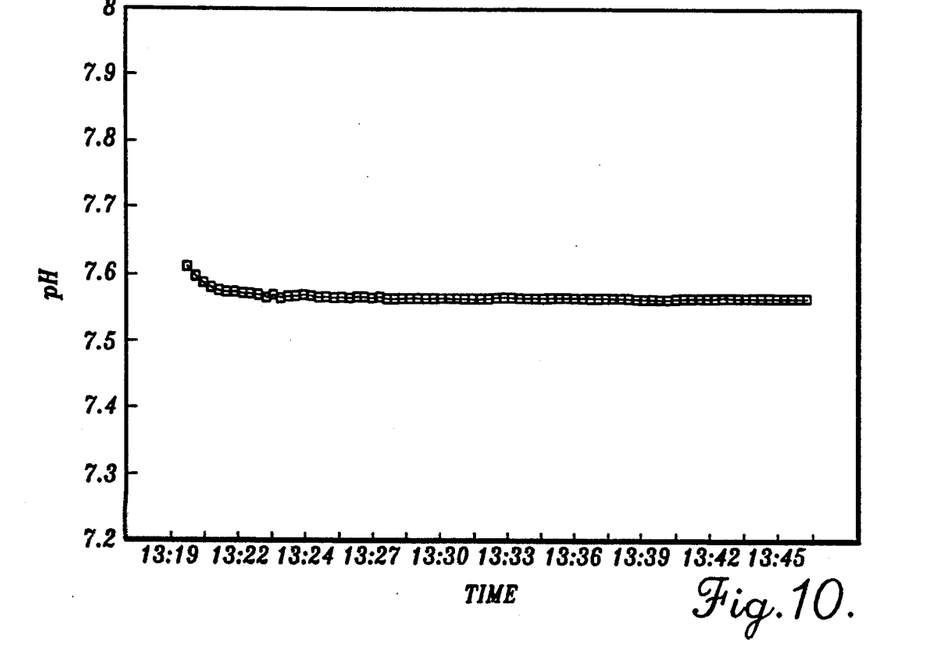
FIG. 10 is a graphical illustration of the effectiveness of the method and system of the present invention to compensate for signal artifacts resulting from movement of the optical waveguide.

Similar results are observed for pH measurements using the method and apparatus of the present invention. FIG. 9 illustrates the discontinuities observed in measurements during intervals of movement of the optical waveguides using prior timing sequences that do not compensate for such movement. FIG. 10 illustrates how the method and system of the present invention are able to compensate for movement of the optical waveguides during sampling intervals.

While the preferred embodiment of the invention has been illustrated and described, it will be appreciated that various changes can be made therein without departing from the spirit and scope of the invention. For example, while a single probe for sensing $CO_2$ concentration, hydrogen ion concentration and $O_2$ concentration has been described, the method and signal control subsystem of the present invention are applicable to probes that measure only $CO_2$ concentration, only hydrogen ion concentration, or both in combination. In addition, the method and system also find use in fiber-optic sensing systems that do not necessarily monitor chemical parameters. For instance, the present invention is compatible with other analog intensity optical sensors, such as those used for sensing physical parameters such as temperature or moisture content. Furthermore, although application specific integrated circuits 83 and 84 have been illustrated in FIGS. 4, 5 and 6 as separate elements, a single application specific integrated circuit carrying out all functions of the two combined can also be employed.

The embodiments of the invention in which an exclusive property or privilege is claimed are defined as follows:

1. A method of compensating for signal artifacts in a sensor for monitoring parameters that includes a distal probe, a source of light signals of a first wavelength, a source of light signals of a second wavelength, at least one optical waveguide for transmitting primary light signals from the source of light signals of a first wavelength and the source of light signals of a second wavelength to the distal probe and for transmitting secondary light signals from the distal probe to at least one sensor for detecting the secondary light signals, respective secondary light signals being derived from respective primary light signals transmitted to the distal probe, wherein the signal artifacts result from changes in the transmission characteristics of the optical waveguide caused by displacement of the optical waveguide, the method comprising:
   sampling the primary light signal from the source of light signals of a first wavelength over a first interval; and
   sampling the primary light signal from the source of light signals of a second wavelength over a second interval, wherein the sum of the first interval and the second interval is less than intervals over which displacement of the optical waveguide occurs.

2. The method of claim 1, wherein the first interval is less than or equal to about 4 milliseconds and the second interval is less than or equal to about 4 milliseconds.

3. The method of claim 1, further comprising the step of digitally demodulating the primary light signals from the sampling steps.

4. The method of claim 3, further comprising the step of using the primary and secondary light signals from the digital demodulation step to determine pH and carbon dioxide levels of blood.

5. The method of claim 1, further comprising sampling the secondary light signals derived from the primary light signal of the first wavelength during the first interval and sampling the secondary light signal derived from the primary light signal of the second wavelength during the second interval.

6. The method of claim 5, further comprising the step of digitally demodulating the secondary light signals from the step of sampling the secondary light signals.

7. The method of claim 6, further comprising the step of using the primary and secondary light signals from the digital demodulation step to determine pH and carbon dioxide levels of blood.

8. The method of claim 1, wherein the primary light signal from the source of light signals of a first wavelength includes light signals of a wavelength in the green region of the visible spectrum and the primary light signal from the source of light signals of a second wavelength includes light signals of a wavelength in the near infrared region of the electromagnetic spectrum.

9. The method of claim 1, further comprising sampling a signal during a third interval on the optical waveguide when the source of light signals of a first wavelength and the source of light signals of a second wavelength are not emitting.

10. The method of claim 9, wherein the third interval is less than or equal to about 4 milliseconds.

11. The method of claim 1, wherein the signal artifacts result from ambient light incident on the probe.

12. A method of compensating for signal artifacts in a system for monitoring parameters that includes a distal probe, a source of light signals of a first wavelength, a source of light signals of a second wavelength, at least one optical waveguide for transmitting primary light signals from the source of light signals of a first wavelength and the source of light signals of a second wavelength to the distal probe and for transmitting secondary light signals from the distal probe to at least one sensor for detecting the secondary light signals, respective secondary light signals being derived from respective primary light signals transmitted to the distal probe, wherein the signal artifacts result from changes in the transmission characteristics of the optical waveguide caused by displacement of the optical waveguide, the method comprising:
   sampling the secondary light signal derived from the primary light signal from the source of light signals of a first wavelength over a first interval; and
   sampling the secondary light signal derived from the primary light signal from the source of light signals of a second wavelength over a second interval, wherein the sum of the first interval and the second interval is less than intervals over which displacement of the optical waveguide occurs.

13. The method of claim 12, wherein the first interval is less than or equal to about 4 milliseconds and the second interval is less than or equal to about 4 milliseconds.

14. The method of claim 12, further comprising the step of digitally demodulating the secondary light signals from the sampling steps.

15. The method of claim 12, or in the secondary light signal from the source of light signals of a first wavelength includes light signals of a wavelength in the green region of the visible spectrum in the secondary light signal from the source of light signals of a second wavelength include light signals of a wavelength in the near infrared region of the electrical magnetic spectrum.

16. The method of claim 15, further comprising sampling a signal during a third interval on the optical waveguide, when the source of light signals of a first wavelength and the source of light signals of a second wavelength are not emitting.

17. The method of claim 16, wherein the third interval is less than or equal to about 4 milliseconds.

18. The method of claim 12, wherein the signal artifacts result from ambient light incident on the probe.

19. A system for controlling the sampling of light signals utilized by a sensor for a monitoring an unknown parameter, the sensor including a distal probe including an optical waveguide, light signals of a first wavelength being absorbed by the probe to an extent dependent upon the unknown parameter, light signals of a second wavelength being transmitted by the probe independent of the amount of the unknown parameter, source of light signals of the first wavelength optically coupled to the probe through a first optical pathway, first photodetector provided in the first optical pathway for detecting the amount of the light signal of the first wavelength emitted by the source of light signals of the first wavelength and producing a first electric signal dependent upon the amount of the light signal of a first wavelength emitted by the light source, second photodetector provided in the first optical pathway for detecting the light signals of the first wavelength attenuated by the probe and producing a second electric signal dependent upon the attenuated light signal of the first wavelength, source of light signals of the second wavelength optically coupled to the probe through the first optical pathway, the first photodetector detecting the amount of the light signal of the second wavelength emitted by the light source and producing a third electric signal dependent upon the amount of the light signal of the second wavelength emitted by the light source, the second photodetector detecting the light signal of the second wavelength transmitted by the probe and producing a fourth electric signal dependent upon the amount of the light signal of the second wavelength transmitted by the probe, the first photodetector also detecting light signals in the first optical pathway when the source of light signals of the first and second wavelengths are not emitting and producing a fifth electronic signal that depends on the detected light signals, and the second photodetector also detecting light signals in the first optical pathways when the source of light signals of the first and second wavelengths are not emitting and producing a sixth electric signal that depends on the detected light signals the system comprising:

first signal-frequency converter connected to the first photodetector for producing a first, third, and fifth frequency signal dependent upon the first, third, and fifth electric signal from the first photodetector;

second signal-frequency converter connected to the second photodetector for producing a second, fourth, and sixth frequency signal dependent upon the second, fourth, and sixth electric signal from the second photodetector;

first counter for sampling the first frequency signal produced by the first signal-to-frequency converter over a first interval and the fifth frequency signal over a third interval;

third counter for sampling the second frequency signal produced by the second signal-frequency converter over a first interval and the sixth frequency signal over the third interval;

second counter for sampling the third frequency signal produced by the first signal-to-frequency converter over a second interval and the fifth frequency signal over the third interval;

fourth counter for sampling the fourth frequency signal produced by the second frequency converter over a second interval and the sixth frequency signal over the third interval, wherein the sum of the first interval, second interval, and third interval is less than intervals during which the optical waveguide is displaced; and timer connected to the first, second, third, and fourth counters and the sources of light signals for controlling the length of the first interval, second interval, and the third interval.

20. The system of claim 19, wherein the sum of the first interval, second interval, and third interval is less than or equal to about 12 milliseconds.

21. The system of claim 19, further comprising a first amplifier intermediate the first photodetector and the first signal-frequency converter and a second amplifier intermediate the second photodetector and the second signal-frequency converter.

22. The system of claim 19, wherein the first and second photodetectors produce a voltage dependent upon the amount of the light signal detected.

* * * * *